US011707381B2

(12) United States Patent
Stowe

(10) Patent No.: US 11,707,381 B2
(45) Date of Patent: Jul. 25, 2023

(54) OCULAR PHARMACEUTICAL APPLICATOR WITH LIGHT-ASSISTED ALIGNMENT AND AIMING

(71) Applicant: Twenty Twenty Therapeutics LLC, South San Francisco, CA (US)

(72) Inventor: Timothy Stowe, South San Francisco, CA (US)

(73) Assignee: TWENTY TWENTY THERAPEUTICS LLC, South San Francisco, CA (US)

( * ) Notice: Subject to any disclaimer, the term of this patent is extended or adjusted under 35 U.S.C. 154(b) by 119 days.

(21) Appl. No.: 17/319,987

(22) Filed: May 13, 2021

(65) Prior Publication Data

US 2021/0353458 A1 Nov. 18, 2021

Related U.S. Application Data

(60) Provisional application No. 63/024,373, filed on May 13, 2020.

(51) Int. Cl.
*A61F 9/00* (2006.01)
(52) U.S. Cl.
CPC .......... *A61F 9/0026* (2013.01); *A61F 9/0008* (2013.01); *A61F 9/0017* (2013.01); *A61M 2210/0612* (2013.01)
(58) Field of Classification Search
CPC ........ A61F 9/0026; A61F 9/0017; A61F 9/00; A61F 9/0008; A61F 2009/00846; A61F 2009/00897; A61M 2210/0612; A61M 2205/3306; A61M 2205/583; A61M 2230/63; A61M 15/008; A61M 11/00; A61M 15/0083; A61M 11/042; A61M 2205/50; A61B 5/4839; A61B 5/1103;
(Continued)

(56) References Cited

U.S. PATENT DOCUMENTS 5,346,132 A * 9/1994 Hahn .................... B05B 7/2472
222/113
5,442,412 A * 8/1995 Frey ....................... A61B 5/486
351/243
(Continued)

FOREIGN PATENT DOCUMENTS

WO 2012072551 A1 6/2012

OTHER PUBLICATIONS

International Search Report and Written Opinion, Application No. PCT/US2021/032325, dated Sep. 14, 2021, 13 pages.
(Continued)

*Primary Examiner* — Kai H Weng
*Assistant Examiner* — Brandon W. Levy
(74) *Attorney, Agent, or Firm* — Haynes and Boone, LLP

(57) ABSTRACT

A fluid dispensing device includes a light source, and a nozzle spaced from the light source. The device also includes a membrane positioned within a beam path of the light source, where the membrane is configured to allow a portion of light from the light source through to the nozzle. The device also includes a fluid chamber positioned between the membrane and the nozzle, where the nozzle is configured to allow a beam of the portion of light to pass through along the beam path, and where the nozzle is further configured to form a stream of fluid expelled from the fluid chamber along the beam path.

13 Claims, 15 Drawing Sheets

(58) Field of Classification Search
CPC . A61B 5/0059; A61B 3/113; A61B 2090/309; A61B 1/0684; A61B 3/0008; A61B 5/6821; A61B 3/14; A61B 2034/2055; A61N 2005/0644; A61N 2005/0648; B65D 47/18; B67D 1/0875; B05B 17/08; B05B 17/085; B05B 11/302; B05B 11/0054

See application file for complete search history.

(56) References Cited

U.S. PATENT DOCUMENTS

| | | | |
|---|---|---|---|
| 5,584,823 A * | 12/1996 | Valberg | A61F 9/0008 222/113 |
| 6,585,698 B1 * | 7/2003 | Packman | G16H 20/17 604/207 |
| 6,777,891 B2 * | 8/2004 | Lys | H05B 47/155 315/291 |
| 8,684,980 B2 | 4/2014 | Hunter et al. | |
| 10,154,923 B2 | 12/2018 | Hunter et al. | |
| 10,583,038 B2 | 3/2020 | Ivri | |
| 2002/0016576 A1 * | 2/2002 | Lee | A61F 9/0008 604/300 |
| 2009/0272818 A1 | 11/2009 | Valpey, III et al. | |
| 2010/0022971 A1 | 1/2010 | Marx | |
| 2011/0106025 A1 * | 5/2011 | Hall | A61F 9/0008 604/298 |
| 2017/0156927 A1 | 6/2017 | Richter et al. | |

OTHER PUBLICATIONS

"Getting Meds into the Eye, 21st Century Style." Christopher Kent, Senior Editor. Published Mar. 15, 2013, available at https://www.reviewofophthalmology.com/article/getting-meds-onto-the-eye-21st-century-style, 5 pages.

"Eye Drug Delivery Firm Eyenovia Sets IPO Range as Plans Come Into Focus." XConomy,Frank Vinluan. Jan. 10, 2018, available at https://xconomy.com/new-york/2018/01/10/eye-drug-delivery-firm-eyenovia-sets-ipo-range-as-plans-come-into-focus/ 3 pages.

\* cited by examiner

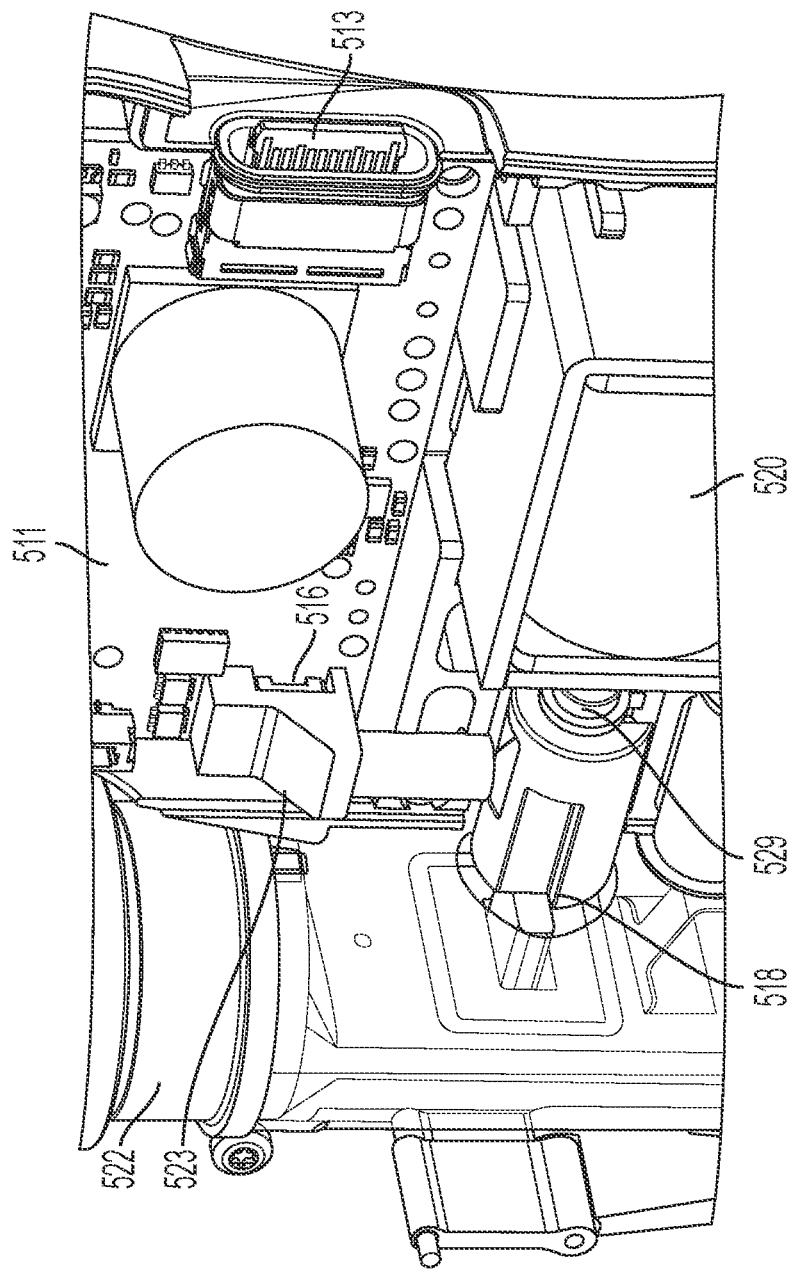

OCULAR PHARMACEUTICAL APPLICATOR WITH LIGHT-ASSISTED ALIGNMENT AND AIMING

CROSS-REFERENCE TO RELATED APPLICATIONS

The present application claims priority to and the benefit of U.S. Provisional Application No. 63/024,373, filed May 13, 2020, the entirety of which is incorporated by reference herein.

TECHNICAL FIELD

The subject matter described herein relates to devices, methods, and systems for delivering a stream of fluid to a patient's eye. This ocular pharmaceutical applicator has particular but not exclusive utility in ophthalmology, for administering pharmaceutical agents to the eye.

BACKGROUND

Delivering medications to a patient's eye presents several challenges. Medication may be delivered by a dropper or a mister. In both cases, blinking of the eye, improper placement of the applicator, or angular misalignment of the applicator can cause some or all of the medication to miss the eyeball and be delivered instead to the patient's eyelids or face, where it may be of little or no therapeutic value and may require cleaning. In addition, many dropper and mister devices are unable to deliver a dose when the device is held horizontally, and may deliver a substantially different dose depending on whether the device is vertical, or at an intermediate angle between vertical and horizontal (e.g., 45 degrees from vertical). Some eye misters include mirrors adjacent to the mist nozzle to aid a user in positioning and aiming the eye mister into the eye. However there can still be some degree of error or discrepancy (e.g., parallax) between the view in the mirror and the actual trajectory of the mist. Standard eye droppers and misters are therefore prone to incorrect and/or imprecise application. Such eye dropper and mister devices may also be difficult or uncomfortable to operate while standing or sitting—particularly for patients with arthritis, back pain, or other conditions.

Many mister devices can only aerosolize liquids with a viscosity similar to water (e.g., around 3 centipoise), whereas liquids with a higher viscosity (e.g., 50 centipoise) must be delivered with a dropper. However, higher-viscosity eye medications have numerous advantages; they may provide increased eye hydration, longer drug residence time, strengthened mucosal adhesion, and the possibility of lipid encapsulation and increased drug loading. Unfortunately, as compared with low-viscosity liquids, higher-viscosity liquids delivered by a may result in longer spreading time to uniformity, ocular blurring, and a sticky sensation accompanied by more difficult eyelash cleaning after a missed targeting. It is therefore desirable to deliver high-viscosity medications as a fine mist, fine sheet, or micro stream delivered accurately to the eyeball, with little or no material landing on eyelids or lashes.

Thus, it should be appreciated that current ophthalmic drug delivery systems have numerous drawbacks, including difficulty delivering a precise or consistent dose, uncertainty about the dose delivered, and difficult cleanup. Accordingly, long-felt needs exist for improved ophthalmic drug delivery systems that address the forgoing and other concerns. The information included in this Background section of the specification, including any references cited herein and any description or discussion thereof, is included for technical reference purposes only and is not to be regarded as subject matter by which the scope of the disclosure is to be bound.

SUMMARY

The present disclosure provides an actuated ocular pharmaceutical liquid applicator with alignment features for helping a user direct a stream of liquid towards the eye. Aiming the drug delivery device towards the eye may involve emitting a narrow beam of light from a light source through the applicator nozzle along the direct streaming axis of the applicator. In some aspects, the narrow beam of light is only visible to the user for a small range of positions and orientations relative to the user's eye to allow the user to confirm whether the nozzle of the applicator is aimed toward an acceptable area of the user's eye for drug application. In other aspects, the alignment features described herein allow the user to aim the nozzle into their eye without parallax. In addition, sensors within the applicator allow for the correct aiming range and position to be sensed relative to the eye, and such information can be communicated to provide feedback to a user by changing the color, or flash pattern of the light source. Thus, the ocular pharmaceutical applicator provides an improved user experience, and may be useful in the treatment of ophthalmic conditions such as glaucoma, dry eye, and red eye (allergic conjunctivitis).

The ocular pharmaceutical applicator disclosed herein has particular, but not exclusive, utility for treatment of ophthalmic conditions such as glaucoma, dry eye, and conjunctivitis.

One embodiment of the present disclosure includes a fluid dispensing device. The fluid dispensing device includes a light source, and a nozzle spaced from the light source. The device also includes a membrane positioned within a beam path of the light source, where the membrane is configured to allow a portion of light from the light source through to the nozzle. The device also includes a fluid chamber positioned between the membrane and the nozzle, where the nozzle is configured to allow a beam of the portion of light to pass through along the beam path, and where the nozzle is further configured to form a stream of fluid expelled from the fluid chamber along the beam path.

In some embodiments, the light source may include an aligned baffle having a first slit width, the nozzle has a second slit width, and the first slit width and the second slit width are less than 400 micrometers (m). In some embodiments, the beam of light is visible to a human eye if the nozzle is aimed at the human eye within a rotational precision below 8.5 degrees when the device is positioned for fluid delivery about 15 mm from the eye. In some embodiments, the nozzle may include two adjacent slits less than 1 mm apart that are positioned and aligned to allow light through to a user so that when the nozzles are aligned to a human eye light through both slits are equally perceived in intensity. In some embodiments, the light source may include a first light-emitting diode (LED). In some embodiments, the light source may include an integrated led surface mount package of two or more single color led dies situated in a single line, where the led surface mount package is configured to change from a first color to a second color without impacting an angle of the light along the beam path. The processor may be configured to determine, using information from the range sensor, whether a range between the nozzle and a human eye is greater than a threshold amount; in response to determining that the range is greater than the threshold amount, change a visual property of the light source to a first value; and in response to determining that the range is less than the threshold amount, change the visual property of the light source to a second value.

The device may further include an applicator body including an actuator, the light source, and an opening aligned with the nozzle. The actuator may be configured to depress the membrane into the fluid chamber thereby causing fluid to be expelled from the fluid chamber through the nozzle. The device may further include a cartridge removably positioned within the applicator body. In some embodiments, the cartridge includes: a fluid reservoir in fluid communication with the fluid chamber; the nozzle; and the membrane.

The cartridge may include a fluid reservoir in fluid communication with the fluid chamber; the nozzle; and the membrane. The applicator body may include at least one brow rest configured to contact a user's eyebrow ridge and at least one cheekbone rest configured to contact a user's cheekbone, such that when the brow rest is contacting the user's eyebrow ridge and the cheekbone rest is contacting the user's cheekbone, the light source is visible to the user's eye through the nozzle. The actuator may include a piston and a head coupled to a distal end of the piston, where the head is configured to contact the membrane in an actuated position, and where the head may include an angled reflective surface positioned with respect to the light source such that the beam from the light source is reflected through the nozzle. The head may include a first opening adjacent to the light source, and a second opening at a distal end of the head, where the angled reflective surface is within the head such that the portion of light enters through the first opening, reflects off the angled reflective surface, and propagates out of the second opening. The applicator body further may include one or more photodetectors, and where the photodetectors are configured to detect a presence of the cartridge based on internal reflection of the light off of the head or the cartridge from the light source. An applicator body may include an activation control, the light source, and the actuator. The cartridge may include the fluid reservoir, the membrane, nozzle, and fluid chamber. The device may include an actuatable nozzle cover coupled to the applicator body and configured to cover the nozzle.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the ocular pharmaceutical applicator, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which:

FIG. 12 is a perspective view of a portion of the ocular pharmaceutical applicator of FIG. 11, according to at least one embodiment of the present disclosure.

DETAILED DESCRIPTION

Figure 1:
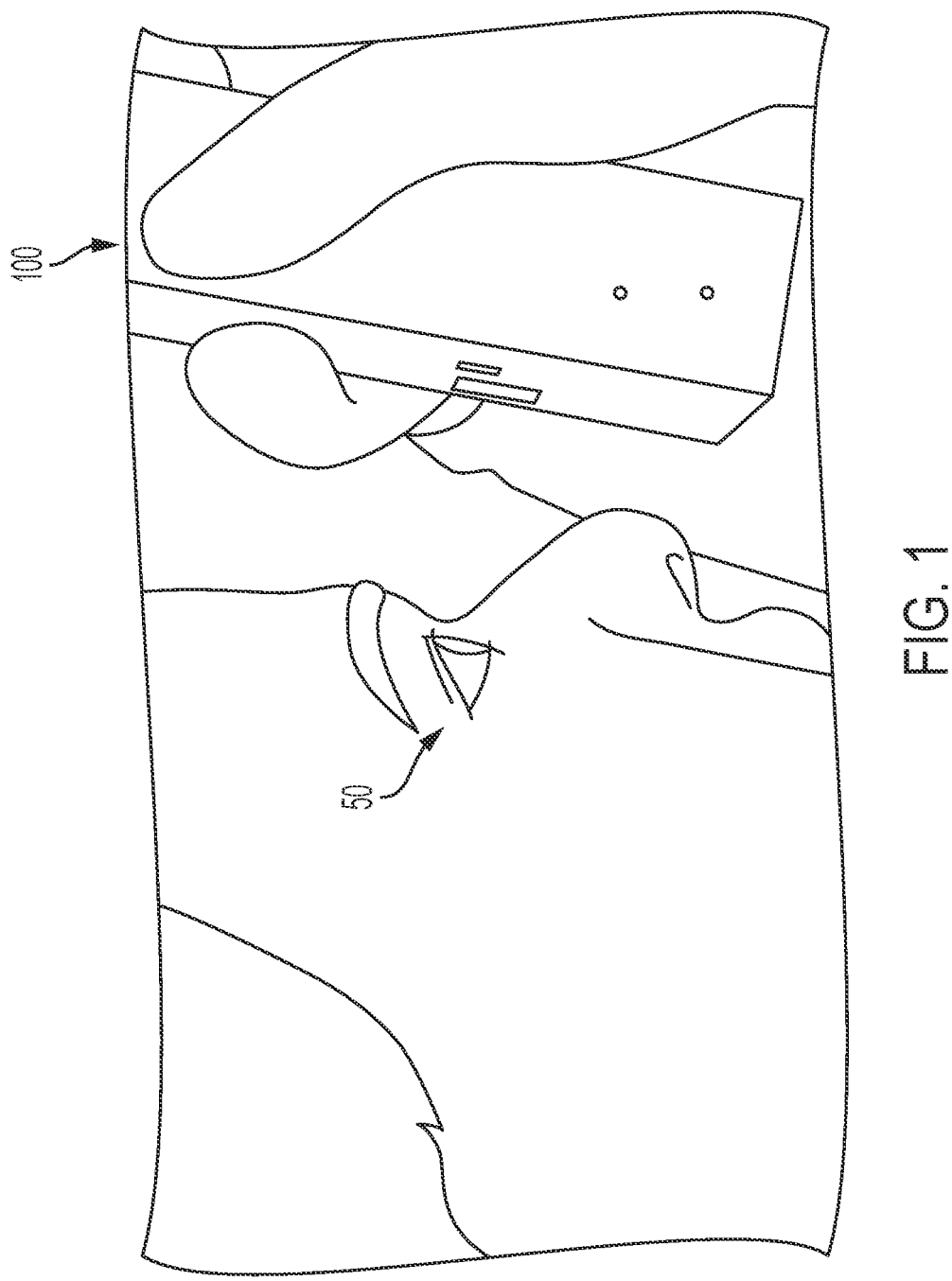
FIG. 1 is a photograph of an example ocular pharmaceutical applicator delivering medication to a patient's eye, in accordance with at least one embodiment of the present disclosure.

In accordance with at least one embodiment of the present disclosure, an ocular pharmaceutical applicator is provided which brings a non-gravitational, orientation-independent ocular drug delivery system into proximity with a patient's eye. The present disclosure provides visual and other cues that help a user align the device towards their eye with a higher precision in both position and orientation than would be possible with a traditional mister or dropper. In an exemplary embodiment, the device incorporates one or more horizontal, slit-shaped nozzle aligned directly with a light source, such as an LED (e.g., aligned without parallax), which permits the user to see the light from the light source only when the nozzle is correctly aligned toward the eye within a range of positions and orientations. The ocular pharmaceutical applicator may not require gravity to function, and thus may function regardless of orientation. The ocular pharmaceutical applicator may include a number of "smart" features such as range detection and blink detection, as well as passive features intended to rest against a user's forehead or cheekbone to aid in proper alignment of the device. The ocular pharmaceutical applicator may be useful for example in the treatment of ophthalmic conditions such as glaucoma, dry eye, and red eye (allergic conjunctivitis).

The ocular pharmaceutical applicator is uniquely designed such that a light source can be directed through the same nozzle which streams medication, i.e. in a path directly in the line of sight through a jetting nozzle. In one aspect, because the fluid loading chamber of the ocular pharmaceutical applicator can be transparent, a single or multicolor LED can be placed directly behind the nozzle of the applicator to allow for direct aiming of the nozzle into the eye. With appropriate aperturing of the light rays, these rays can be confined to a small angular range that can directly pass through the slit nozzle such that the light rays from the light source are only visible when correctly aligned with the eye. A user will then only see the colored LED light with high visual acuity over their eye's fovea color receptive region within a narrow aiming range such as +/−10 degrees, which assists the user in correctly aiming the device towards the eye, assuming the LED brightness is appropriately chosen.

In some embodiments, optical proximity sensors are employed such that the distance to the eye can be estimated. If the applicator distance is too far (e.g., more than 20 mm from the eye), the light source may be controlled to change in color or in illumination pattern (e.g., blinking, strobing, pulsing, solid) for example. Further, if the applicator is close enough to be in range it can be changed from a first color to a second color. For example, blue and orange may be a common colorblind-friendly palette. However, any suitable color and color combination can be used. An RGB LED can be used, which is capable of a wide color gamut by adjusting relative currents to each LED. The intensity of the LED can also optionally be flickered or strobed to be used in a similar manner to a blink-defeating signal in a flash camera. Thus, through color changing and time domain changing signals, range, alignment, and aiming can be communicated to the user while they are holding the device, greatly improving the ease of use of the device.

The present disclosure aids substantially in ophthalmic drug delivery, by improving the ability of even inexperienced users to place the device at a desirable position, range, and orientation to deliver drugs to their own eyes. This improved self-aiming ability transforms an imprecise, unreliable manual procedure into a reliable, repeatable, machine-assisted procedure, without the normally routine need to lie down, try multiple times, or have a second person dispense the medication. This unconventional approach improves the functioning of the ophthalmic drug delivery system, by enabling a user to self-administer ophthalmic drugs with a high rate of success.

These descriptions are provided for exemplary purposes only, and should not be considered to limit the scope of the ocular pharmaceutical applicator. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. The examples described herein are provided for purposes of illustration, and are not intended to be limiting.

FIG. 1 is a side view of an example ocular pharmaceutical applicator 100 delivering medication to a patient's eye 50, in accordance with at least one embodiment of the present disclosure. As mentioned above, in some embodiments, the ocular pharmaceutical applicator 100 is configured to produce a stream of an ophthalmic fluid such that the applicator 100 can be used in a horizontal configuration. In some aspects, the stream of fluid may be referred to as a microstream. Thus, the user can apply the fluid without leaning back to allow gravity to direct the fluid into the patient's eye 50. In order to deliver a proper dose, it is useful for the ophthalmic drug dispenser or ocular pharmaceutical applicator 100 to be held in a proper position and orientation with respect to the target eyeball 50. The ocular pharmaceutical applicator 100 provides several features that reduce the burden of this aiming process, which would otherwise be difficult even for experienced users, as described below.

Figure 2:
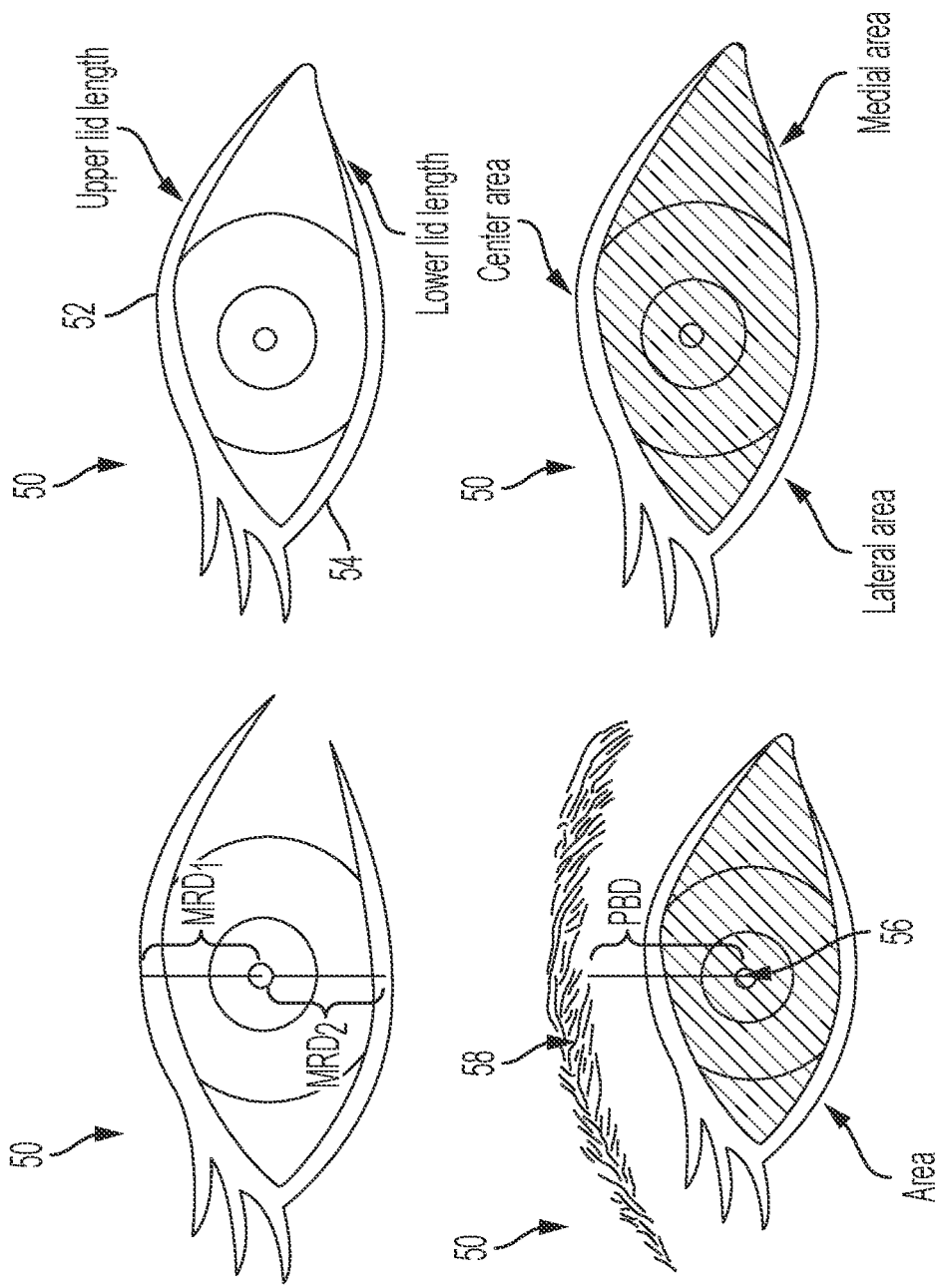
FIG. 2 is a diagrammatic representation of exemplary drug delivery zones for a human eye.

FIG. 2 is a diagrammatic representation of exemplary drug delivery zones for a human eye 50. MRD1 and MRD2 are the "margin reflex distances" between the pupil and eyelids (upper 52 and lower 54, respectively) when the patient is looking straight ahead at a light source. MRD1 and MRD2 are typically around 4 mm PBD is the pupil-to-brow distance between the center of the pupil 56 and the brow 58. Because the eyelids 52, 54 form a shape that is elongated in the horizontal dimension and shortened in the vertical dimension, there is more room for error in the placement of medications in the horizontal direction than in the vertical direction. For reasons of comfort and vision, it is also desirable to dispense a medication as evenly as possible across the eye 50. Therefore, in some embodiments, the nozzle of the ocular pharmaceutical applicator is a horizontal slit that aims the medication in a horizontal line across the horizontal dimension of the eye 50, in order to maximize spreading across the eye surface while simultaneously reducing the amount of material that misses the eyeball 50 and contacts the eyelids 52, 54 or skin.

Figure 3:
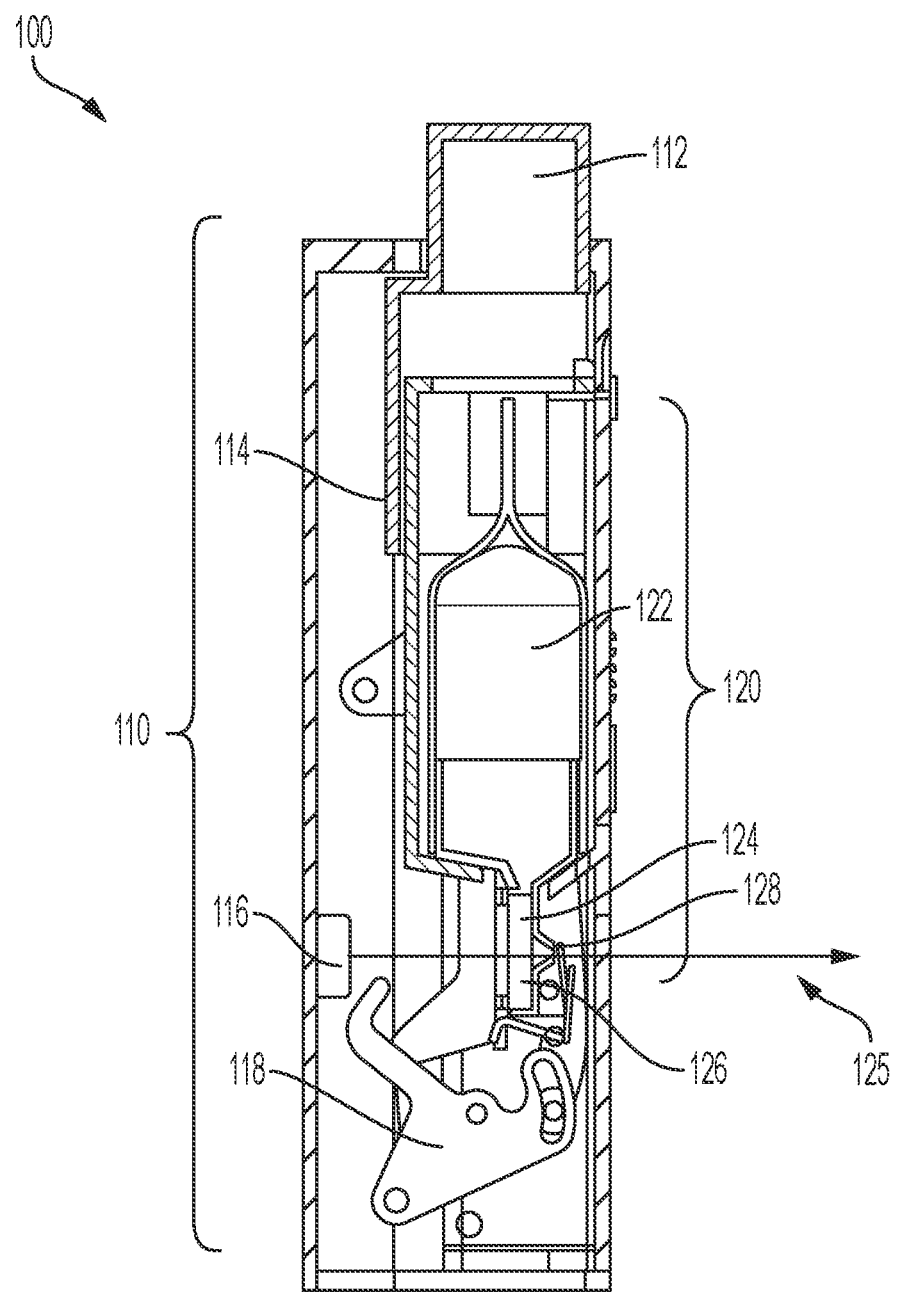
FIG. 3 is a cross-sectional side view of an example ocular pharmaceutical applicator according to at least one embodiment of the present disclosure.

FIG. 3 is a cross-sectional side view of an example ocular pharmaceutical applicator 100 according to at least one embodiment of the present disclosure. The ocular pharmaceutical applicator 100 includes an applicator body 110 comprising an activation button 112, a sliding actuation mechanism 114, a light source 116, and an actuation hammer 118. The ocular pharmaceutical applicator 100 also includes a replaceable cartridge 120 that comprises a drug reservoir 122, a transparent, elastically deformable wall or membrane 124, a fluid chamber 126, and a nozzle 128. In an example, when the removable cartridge 120 is in place and a power switch is turned on, the light source 116 draws power from a power source (e.g., a battery) and shines a light beam 125 through the membrane 124 and nozzle 128, such that the light beam 125 is visible to a human eye if the nozzle 128 is correctly pointed at the eye. When the activation button 112 is pressed, the sliding actuation mechanism 114 descends, such that the actuation hammer 118 is cocked and then released, after which the actuation hammer 118 strikes the membrane 124, forcing any fluid in the fluid chamber 126 to be expelled through the nozzle 128. When the activation button 112 is released, the hammer 118 releases the membrane 124, creating negative pressure in the fluid chamber 124, which draws another dose of fluid from the drug reservoir 122 into the fluid chamber 126.

In an example, the nozzle 128 comprises a slit that is narrow enough that surface tension holds the liquid in place against gravity, shaking, etc., while still permitting a tight stream to be delivered to the eye with sufficient volume to dispense a required dose of the medication. In an example, the light source 116 comprises an LED aligned with a dispensing axis of the nozzle 128 and spaced from the nozzle 128. In the embodiment shown in FIG. 3, the light source 116 may be described as being behind the nozzle 128.

Figure 4:
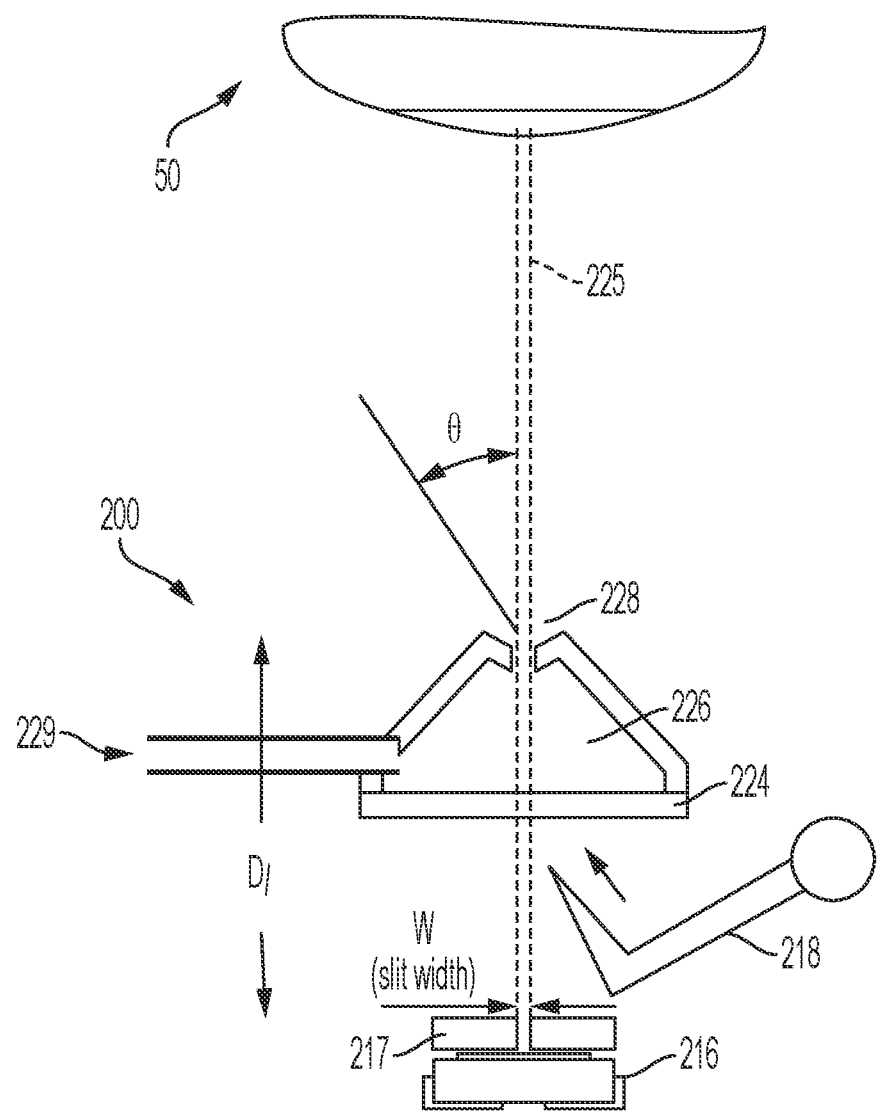
FIG. 4 is a diagrammatic view of an example drug delivery mechanism of the ocular pharmaceutical applicator according to at least one embodiment of the present disclosure.

FIG. 4 is a diagrammatic view of an example drug delivery mechanism 200 of an ocular pharmaceutical applicator according to at least one embodiment of the present disclosure. The mechanism includes a light source 216 configured to emit a light beam 225 through a baffle/collimator 217, a nozzle 228, a transparent, elastically deformable wall or membrane 224, a fluid chamber 226, a refresh channel 229, and a rotational strike arm 218 or actuation hammer. In an example, the light source 216 is a SMD RGB LED package. To ensure correct alignment of the ocular pharmaceutical applicator, it is advantageous to mount the LED 216 behind the fluid chamber 226 and membrane 224, and in line with the nozzle 228 but outside the range of motion of the striker 218 used to actuate fluid through the nozzle 228, i.e. in the direct line of sight of the nozzle spray.

The angular range or spread of the light beam 225 is determined in part by the width and thickness of the aperture slit W and offset distance of the nozzle 228 to the LED aperture slit D1. It may be desirable that this range be narrower than the acceptance angle for aiming the ocular pharmaceutical applicator towards the eye's fovea and the natural acceptance angle of myopic rays to the fovea.

The strength of the light intensity may be adjusted such that ambient light will dominate the signal received by the fovea under normal conditions unless the LED signal falls directly over the eye's fovea color center (cones), which has an acceptance angle of approximately +/−2 degrees for the highest visual acuity instead of the black and white (rods) which has a much larger acceptance angle (~120 degrees). In practice this may mean that the current used to power the light source can be very low, in the range of 10-20 mA, and can function with millicandela level outputs.

In an example, for a typical fovea of about 2.5 mm in radius (a roughly circular shape) and a human eye focal length of about 17 mm, the angular acceptance range (for rotation of the device, denoted by angle of rotation ⊖ in FIG. 4) of the light to hit the fovea is roughly +/−8.36 degrees. This value is for illustrative purposes only, and the exact value for the angular acceptance range may depend upon many additional parameters. If the light is placed on the opposite side of an applicator (opposite that closest to the eye), and the applicator is roughly 15 mm wide and is placed 15 mm from the surface of eye, the total distance from the LEDs to the eye is 30 mm Because there are only 15 mm to the eye from the nozzles, this 8.36 degree angle will lead to an off center strike distance on the human eye of only +/−2.2 mm Since MRD1 and MRD2 are typically about 4 mm in a human adult, there is approximately 2 mm margin in aiming error. An angle of +/−8.5 degrees may be acceptable. By positioning a metal laser-patterned defined aperture over the SMD RGB LED package, the natural angular tolerance of the RGB LED may be significantly less than +/−8.3 degrees. For a nozzle slit width of 300 micrometers (μm) and baffle/collimator slit width of 300 μm and a distance D1 of roughly 10 millimeters (mm) or greater, the natural angular range of LED light that makes it through the nozzle is approximately +/−0.03 radians or +/−1.7 degrees and thus the angular misalignment tolerance for aiming the nozzles towards the eye is limited only by the diameter of the human fovea. Other baffling slit widths both larger and smaller may be used, including for example values between about 100 um and about 500 um.

In practice, user perception of the light source alignment may be even more sensitive than these calculations suggest. For example, increased brightness, as well as more crisp visual acuity when the light source is aimed correctly may be perceived by the user such that the user can more precisely orient and aim the applicator toward the center of the eye. Thus, an LED placed at an adequate distance behind the nozzle and aimed directly through the nozzle provides a reliable targeting user interface for the ocular pharmaceutical applicator.

Figure 5:
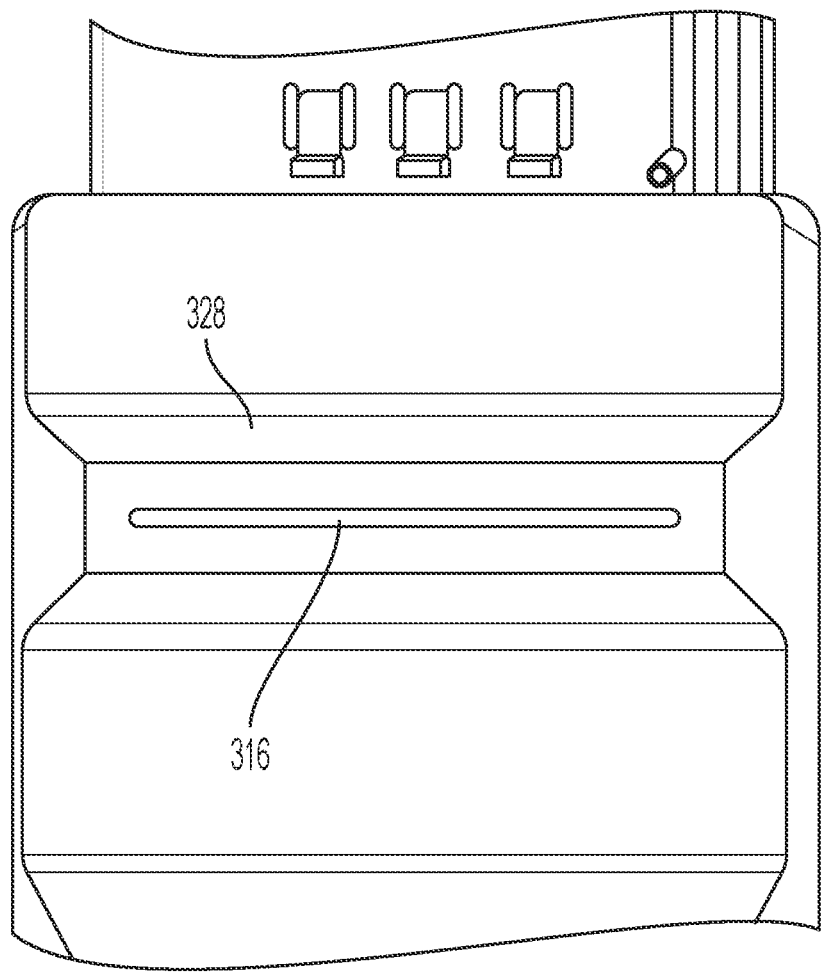
FIG. 5 is a front view of an example nozzle with an LED shining through it in accordance with at least one embodiment of the present disclosure.

FIG. 5 is a front view of an example nozzle 328 with an LED 316 shining through it in accordance with at least one embodiment of the present disclosure. Light is baffled so it is visible only through the slit of the nozzle 328. In some embodiments, the LED is 316 inline with the slit. In other embodiments, the LED 316 may be positioned above or below the plane of the slit, and an angled mirror inline with the slit may reflect the light through the nozzle 228.

Figure 6A:
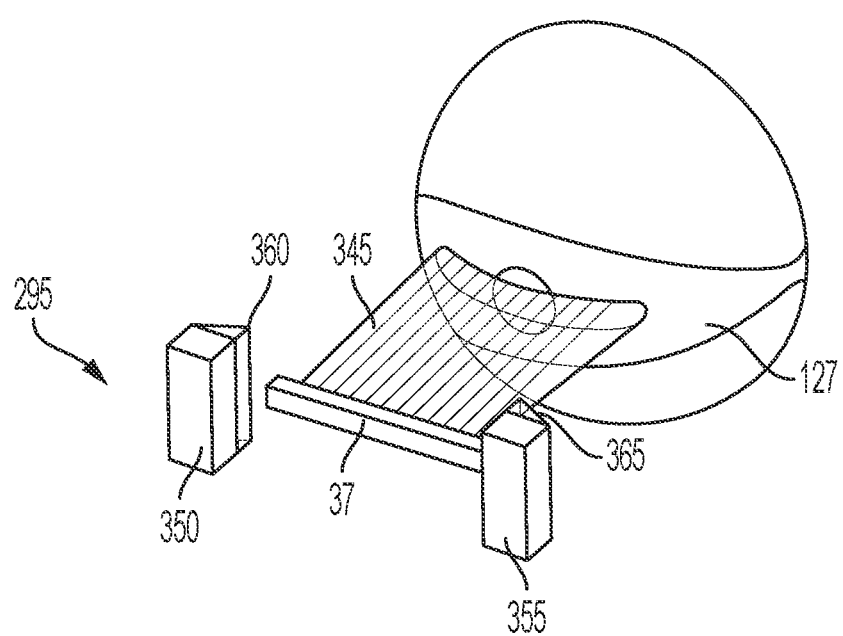
FIG. 6A is a perspective view of a blink detection and proximity sensing assembly in accordance with at least one embodiment of the present disclosure.
Figure 6B:
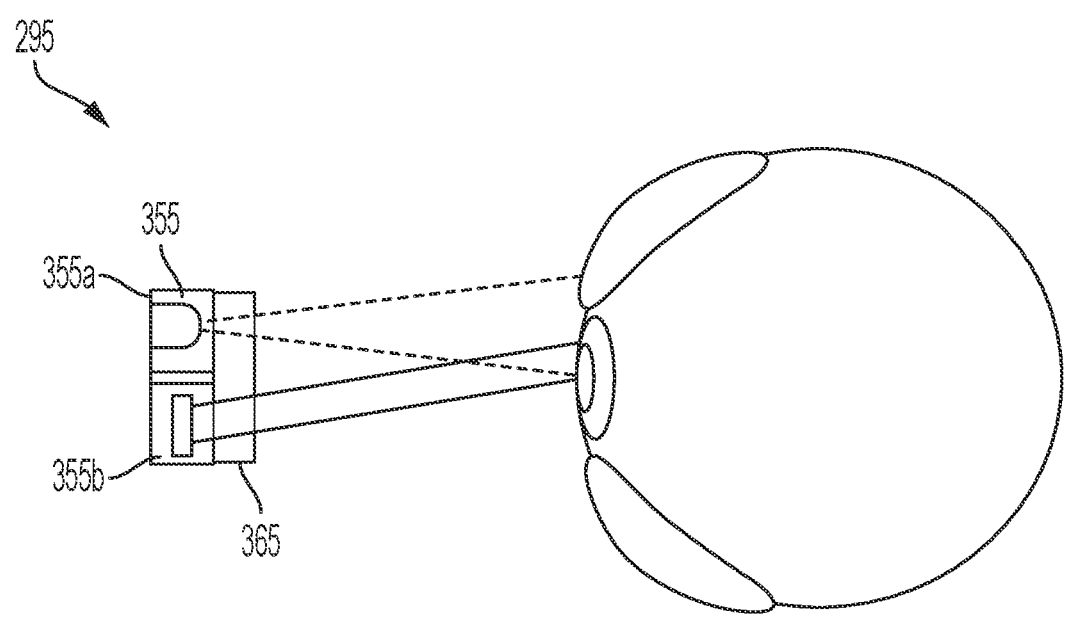
FIG. 6B is an elevation view of a blink detection and proximity sensing assembly in accordance with at least one embodiment of the present disclosure.

Furthermore, if optical proximity sensors are employed, the distance to the eye can be estimated. In this regard, FIGS. 6A and 6B illustrate an embodiment of a nozzle 37 of a drug delivery mechanism that includes blink detection and proximity sensing. In this regard, proximity sensors may be used to measure the distance to the eye, detect blinks, or both. A blink detector 295 includes two reflective proximity sensors 350 and 355 in a paired arrangement to verify proper eye targeting and to detect eye blinks. In some embodiments, sensors 350 and 355 are positioned on either side of the nozzle 37. In some embodiments, each sensor 355 and 350 includes a LED and photodiode (illustrated as 355a and 355b in FIG. 6B). In some embodiments, the two sensors 350 and 355 are optical proximity infrared sensors that are configured to detect the presence of the FIG. and determine if a blink has occurred. In some embodiments, the sensors 350 and 355 are reflective proximity sensors with lensed light collection and surface mount technology packaging. In some embodiments, the sensors 350 and 355 are OPB733TR sensors from TT Electronics of Carrollton, Tex., United States of America or HSDL-9100 sensors from Avago Technologies of San Jose, Calif., United States of America, but the sensors 350 and 355 may be any LED and photodiode detector. In some embodiments, the sensors have a molded package surface above the top surfaces of their micro lenses so as to provide a convenient surface onto which a micro prism 365 of approximately 30 degrees angle can be mounted. Generally, the sensors 350 and 255 register a balanced threshold signal indicating alignment to the eye 127 and a distance that is within a target range to the eye 127. In some embodiments, the target range to the eye is about 10 mm to about 30 mm. In some embodiments, L is between about 15 mm and 20 mm.

Reflections from the eye 127 can be detected in the 15-25 mm range but predicted spatial orientation and alignment is often inaccurate when based on information from only one photo proximity pair (i.e., LED and photodiode combination). As such, the positioning of the two sensors 350 and 355 at an equal distance from the nozzle 37 results in off-axis reflected signals that can be compared. Typically, users can horizontally orient a device very accurately and can align the horizontal position accurately but suffer from poor judgement in terms of vertical angular and vertical spatial targeting. Moreover, the eye 127 typically has only 8-9 mm of clearance between the eyelids, but 18 mm of clearance over the horizontal sclera of the eye 127. As such, the clearance over the horizontal sclera is much greater than the clearance between the eyelids. In addition, because of the natural curvature of the eye (typically a radius of 11.5-12.5 mm), it is difficult to direct most of the light normal to the eye 127 to optimize reflected signal intensity without mounting photo proximity sensors on a tilted or curved substrate, which would result in increased cost. As such, the blink detector 295 also includes micro prisms 360 and 365 that direct the light normal to the scleral and corneal surface of the eye 127, and the reflection of the interrogation beams can be increased significantly when the eye 127 is in the optimal distance and position normal two their path. Thus, the sensors 350 and 355 and the micro prisms 360 and 365 can be used as an electronic means to detect optimal alignment of the nozzle 37 to the eyeball as well as blink detection.

When the nozzle 37 includes a plurality of openings, for example 8-10 openings roughly 300 μm in diameter and adequately spaced apart to allow for nozzle cone angle and low hydraulic losses, the dimension 120a of the array is approximately 14 mm. As such and in some embodiments, the sensors 350 and 355 and respective micro prisms 360 and 365 are separated by about 18 mm. However, the spacing of the sensors 350 and 355 may be based on the size of the cartridge and nozzle 37. For example, a single horizontal slit nozzle may allow for a separation of 16 mm. In some embodiments, the arrangement allows an optimal micro prism angle α for a glass (n=1.5) that maximizes the scattering of the reflected light back into the photodiode detectors of the sensors 350 and 355. The associated calculated optimal prism angle of close to 30 degrees, which is a commonly available low cost angled prism. Because the prism angle is perpendicular to the arrangement of the photodiode detector, there is no danger of back reflection off of the prism surfaces back into the photodiode detector from the LEDs. In some embodiments, the micro prisms 360 and 365 are omitted.

In the vertical direction, as long as the divergence of the rays of the LED are in the range of +/−20 degrees, which is very typical, an adequate signal will be obtained as long as the light is not directed to high or load towards the upper or lower eyelids, as illustrated in FIG. 6B.

If the applicator distance is too far (e.g., greater than 20 mm) the light source can change in color to blinking red or yellow for example, and if the device is close enough to be in range it can be changed to green or blue. Blue/orange may be used as a colorblind-friendly palette. Blue/red could be used as an alternative. However, any suitable color and/or color combination could be used, including green, violet, yellow, white, etc.

Figure 7B:
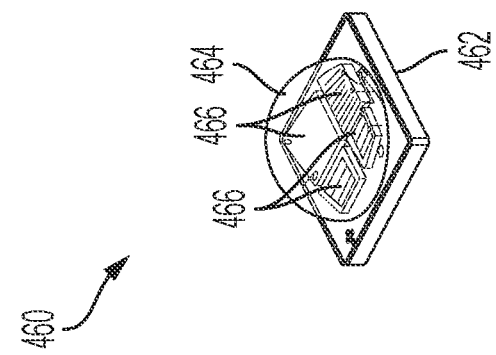
FIG. 7B shows an LED configuration for use in the ocular pharmaceutical applicator in accordance with at least one embodiment of the present disclosure.
Figure 7A:
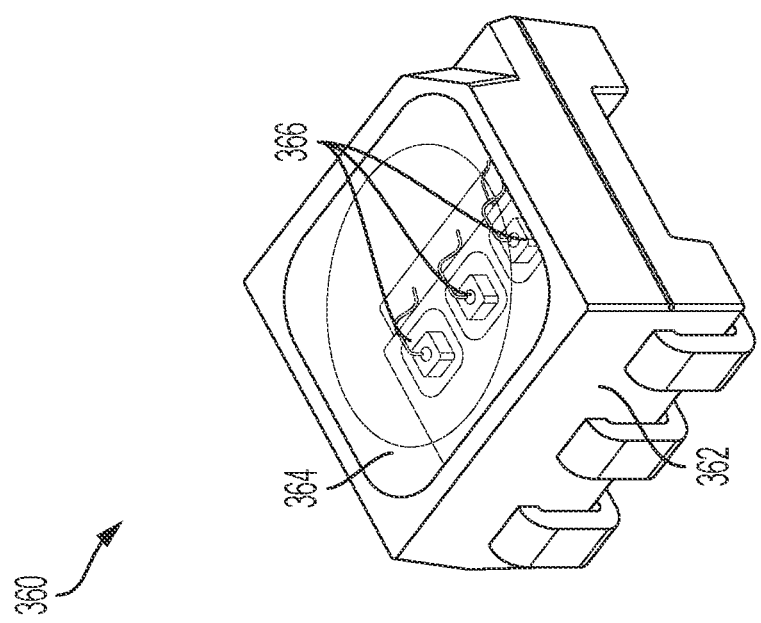
FIG. 7A shows an LED configuration for use in the ocular pharmaceutical applicator in accordance with at least one embodiment of the present disclosure.

FIG. 7A shows an LED configuration 360 for use in the ocular pharmaceutical applicator in accordance with at least one embodiment of the present disclosure. Most multicolor LED packages such as monolithic SMD RGB LEDs may include three individual red, green, and blue LEDs mounted in a signal monolithic package. This may not satisfy the alignments necessary for the ocular pharmaceutical applicator, and thus the detailed packaging specifications for a desirable RGB LED are further defined and narrowed as follows.

In the example shown in FIG. 7A, the LED package 366 includes a case 362 with a transparent or translucent cover 364, and a row of multi-color LEDs 366 (e.g., three LEDs) that create a line of illumination rather than a spot. One such example is the LRTB GVTG from Osram. By changing the relative current through each LED 366, a wide variety of colors in an RGB LED can be programmed with simple LED drivers. Intensity can be modulated with high frequency pulse width modulation to change the ON duty cycle, or the intensity can be modulated directly by programming the drop current across each of the three color LEDs mounted in a single package. In an example, discrete RGB LED chips are arranged inside the package along a single line, and the transparent cover 364 is a flat-topped diffuse white packaging for optimized uniformity across a line. It may be advantageous that all three individual LEDs are mounted in a single row or column (rather than two-dimensionally), and that the long dimension of the row be aligned with the long dimension of the slit of the nozzle such that a single slit aperture placed over the package will impact the amplitude of the light equally and the horizontal slit will collimate the light of each color along the same line as shown for example in FIG. 4.

It may also be desirable to have a diffuse flat lens package style that provides a uniform source that allows for an easy mountable flat black aperture directly over the LED package. A white scattering back reflector surface is further optimal to allow for diffuse uniform light across the whole extent of the package. In an example, the length of the package along the directions that all 3 LED chiplets are oriented is more than 2 mm.

FIG. 7B shows another LED configuration 460 for use in the ocular pharmaceutical applicator in accordance with at least one embodiment of the present disclosure. The LED 460 includes several single-color LEDs 466 arranged in a two-dimensional array, as well as a curved, clear lens 464, all mounted on a case 462. It will be understood that the arrangement shown in FIG. 7B may lead to a difference in the angular ranges of the beams formed by the different colored LED's through the slit of a horizontal nozzle and thus a package in accordance with 7A.

In some aspects, the light source of the applicator devices described herein may have a brightness of ~20 cd*(3E−2)^2~18 mcd or more. Examples of low cost RGB LED packages that can be incorporated include for example the LRTB GVTG from Osram.

In other aspects, external parts of the applicator body that come in contact with the patient's skin are made of polycarbonate overmolded with medical-grade TPSIV, silicone, or polyurethane.

Figure 8:
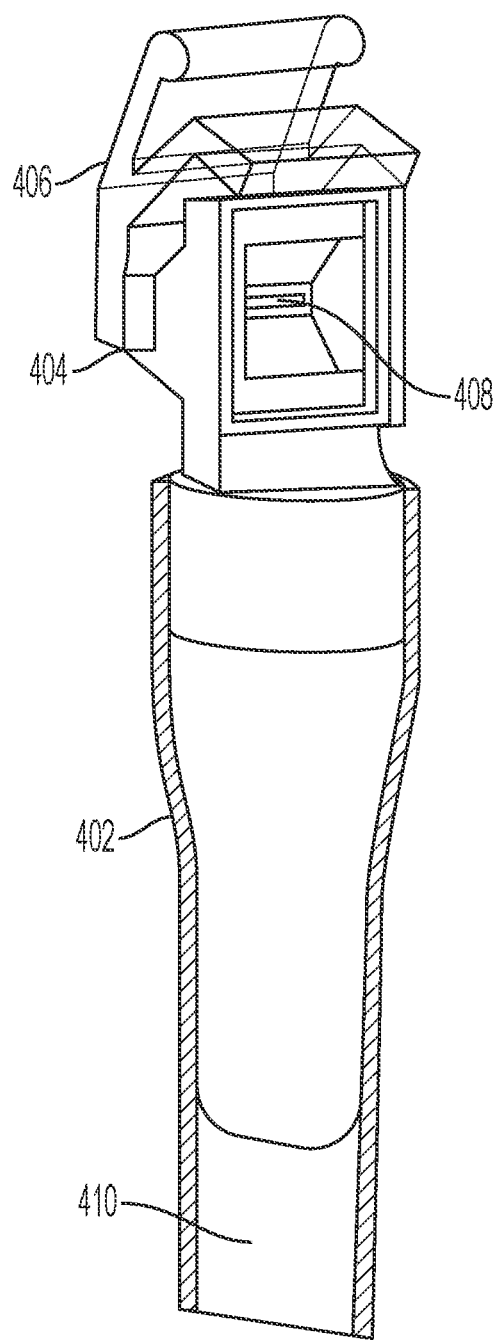
FIG. 8 is a perspective view of a reusable, replaceable ocular pharmaceutical applicator cartridge, in accordance with at least one embodiment of the present disclosure.

FIG. 8 is a perspective view of a reusable, replaceable ocular pharmaceutical applicator cartridge, in accordance with at least one embodiment of the present disclosure. The ocular pharmaceutical applicator cartridge is configured to be placed within an ocular pharmaceutical applicator, which comprises one or more components to expel the fluid from the cartridge. The cartridge includes a transparent or translucent membrane 404, a nozzle 408, a nozzle cover 406, a fluid chamber, a drug reservoir 402, and a label area 410. The drug reservoir 402 is in fluid communication with the fluid chamber, which may be defined in part by the nozzle 408 and the membrane 404, as described above. The size of the opening of the nozzle 408 may be small enough such that the surface tension of the pharmaceutical fluid to be administered retains the fluid within the fluid within the fluid chamber 402 without substantially leaking through the nozzle 408.

In an example, the nozzle 408 and nozzle chamber are made of molded, gamma-safe polypropylene, the drug reservoir is made of blow-fill-seal polypropylene and includes one or more medical grade, sterile polypropylene filters with 0.1-0.2 um pore size. However, any suitable material may be used. Functional coatings on drug-contacting portions may include silver coatings, other antimicrobial coatings, and hydrophilic surfaces, and antimicrobial properties, whereas the nozzle may include a fluoropolymer hydrophobic medical device coating. External surface films may be non-functionalized, including a cartridge pull tab, cartridge flap seal (shipping seal), label, barcode, and data matrix made of 3M medical-grade LSE tapes. The transparent, flexible membrane may for example be made of PETE, PTFE, or polypropylene. Inside surfaces of the cartridge, including the membrane, that come in contact with the medication may include a medical-grade hydrophilic coating.

Some embodiments do not include a replaceable cartridge, but rather incorporate all the components of the replaceable cartridge into the applicator body. In other embodiments, some of the components of the cartridge shown in FIG. 8, but not all, are incorporated into the applicator body. For example, in some embodiments, the nozzle, fluid chamber, and the elastomer cover are part of the applicator body, while the drug reservoir is part of the removable cartridge.

Figure 9:
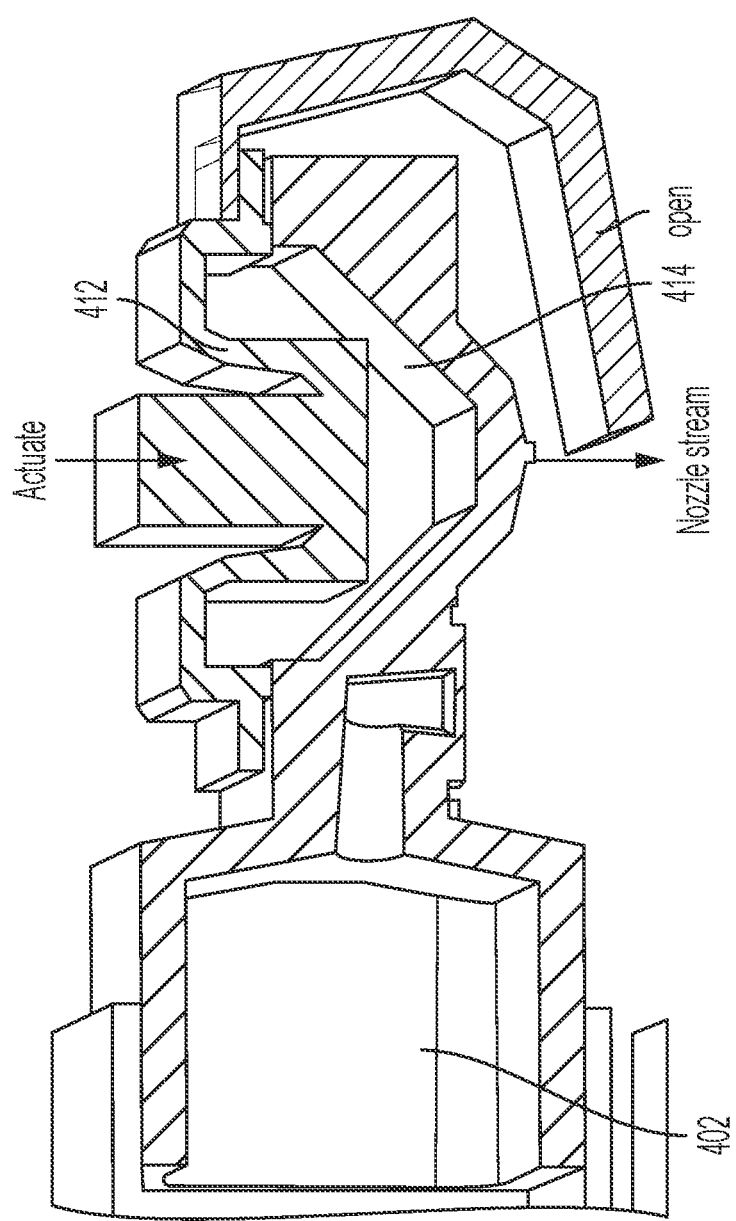
FIG. 9 is a perspective view of the dispensing portion of the ocular pharmaceutical applicator of FIG. 10 in an actuation configuration, in accordance with at least one embodiment of the present disclosure.
Figure 10:
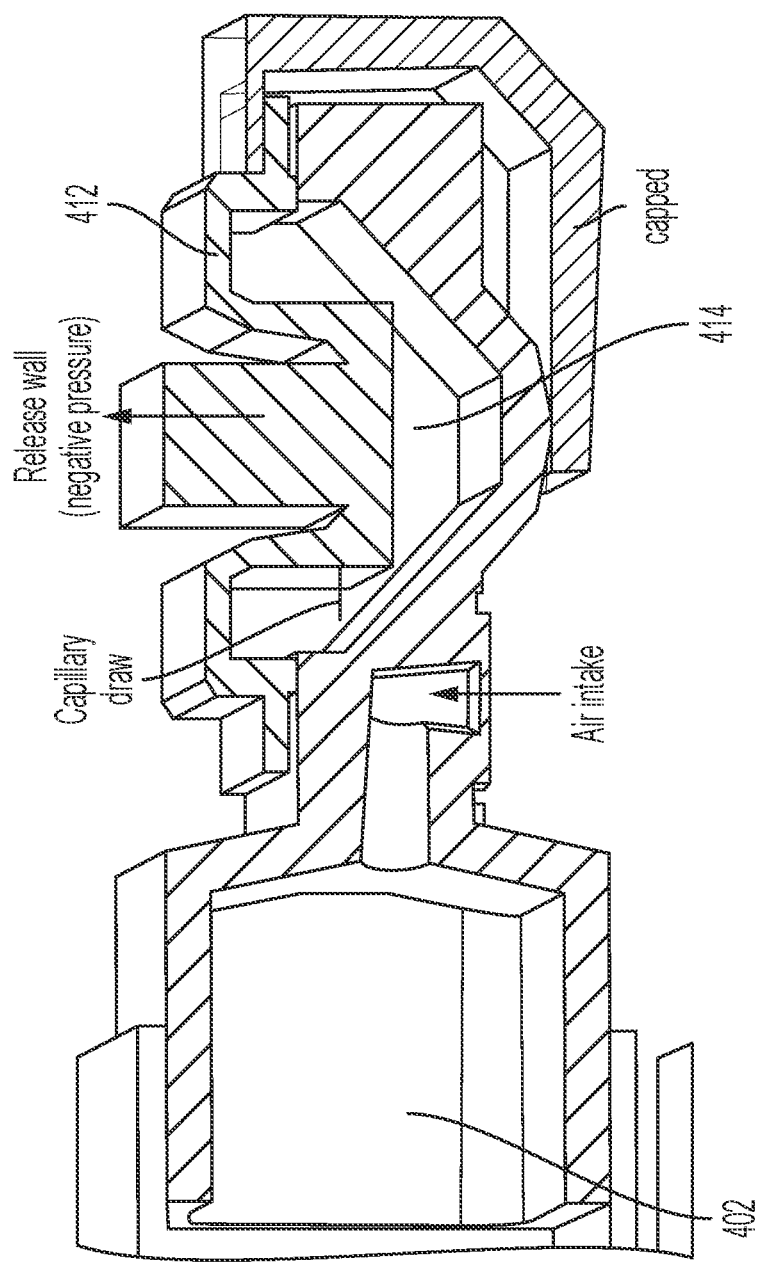
FIG. 10 is a perspective view of a portion of the ocular pharmaceutical applicator of FIG. 10 in a cap and reload configuration, in accordance with at least one embodiment of the present disclosure.

FIGS. 9 and 10 show a dispensing portion of an ocular pharmaceutical applicator during various stages of use. In some aspects, the ocular pharmaceutical applicator shown in FIGS. 9 and 10 may comprise a removable ocular pharmaceutical applicator cartridge placed within an applicator body.

FIG. 9 is a perspective view of a portion of the ocular pharmaceutical applicator in an actuation stage, in accordance with at least one embodiment of the present disclosure. The cap or cover is open, and the transparent, elastically deformable wall or membrane 412 is being depressed (e.g., by the actuation hammer of FIG. 4), forcing fluid out of the nozzle chamber 414 in a stream. In this state the light source may be turned off to save power as the hammer blocks it. It should be noted that the aiming LED light source also provides a convenient way of measuring the presence of the hammer in this activated state by tracing internal reflections of the light inside the applicator and putting a photodiode there. Thus the presence or absence of the cartridge, or the presence or absence of the hammer location, could also be sensed by utilizing the aiming LED.

FIG. 10 is a perspective view of a portion of the ocular pharmaceutical applicator in a cap and reload configuration, in accordance with at least one embodiment of the present disclosure. The cap has been replaced, and negative pressure on the elastically deformable wall or membrane 412 (e.g., from withdrawal of the actuation hammer of FIG. 4) draws fluid into the nozzle chamber 414 (e.g., from the drug reservoir via the refresh channel).

The spray profile provided by the devices described herein may have various geometrical or spatial characteristics that are beneficial for ophthalmic therapeutic applications. In an example, the spray profile at such close ranges is substantially elliptical, with a width less than the width of the eye, which allows the spray to cover the eye in a thin coating. It may be desirable for the range between nozzle and eyeball to fall between, for example, 10 and 20 mm, in some embodiments. In that regard, the nozzle may be sized, shaped, and otherwise structurally configured to form a wide spray pattern of a fluid having a particular viscosity within a particular application range or distance.

Figure 11:
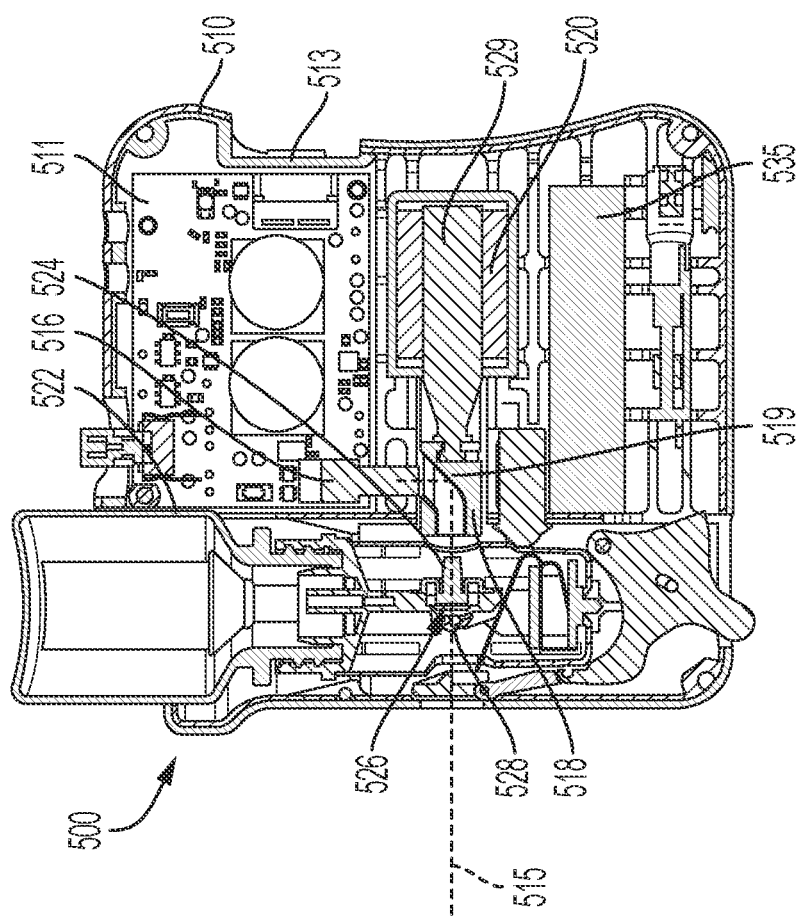
FIG. 11 is a cross-sectional view of an example ocular pharmaceutical applicator according to at least one embodiment of the present disclosure.

FIG. 11 is a diagrammatic view of an ocular pharmaceutical applicator, according to an embodiment of the present disclosure. Similar to the embodiments described above, the applicator includes a housing or enclosure 510 that contains a reservoir 522 containing a pharmaceutical fluid, an actuator 520, a battery 535 and a circuit assembly 511 comprising a connector 513 and a light source 516 mounted to a substrate. In the illustrated embodiment, the actuator 520 comprises a solenoid 529 configured to actuate, such that a piston head 518, which may also be referred to as a light guide, impinges or strikes the membrane 524 to expel the fluid in the chamber 526 out through the nozzle or slit 528. As similarly described above, the chamber 526 can be filled with the pharmaceutical fluid from a drug reservoir 522. In some embodiments, the drug reservoir 522 includes a replaceable cartridge or bottle that includes the chamber 526, membrane 524, and nozzle 528. The head 518 of the solenoid is sized and shaped to deform the membrane 524 into the chamber 526. It will be understood that, in the embodiment of FIG. 11, the solenoid 529 is aligned with the stream axis of the nozzle 528. Accordingly, the light source 516 is positioned above the head 518 and is configured to direct a beam of light toward a diagonal surface 519 of the head 518. The diagonal surface 519 is reflective, and is angled such that the beam of light is reflected through the slit 528 along a beam path. The light emitted from the light element 516 is reflected down toward the reflecting surface 519 by a light directing element, which will be described below. In the illustrated embodiment, the diagonal surface 519 is oriented at an angle of 45 degrees relative to the dispensing axis 515 of the slit 528, with the light source 516 positioned directly below the diagonal surface 519. However, other configurations are also contemplated. For example, the diagonal surface 519 may be oriented at angles other than 45 degrees, both greater and smaller. Additionally or alternatively, the light source 516 may be offset from the head 518 of the solenoid 529 such that the axis of the light source 516 is oblique to the dispensing axis of the nozzle 528.

FIG. 12 is a perspective view of a portion of the pharmaceutical applicator 500 shown in FIG. 11. As shown in FIG. 12, the light directing element 523 may include a diagonal mirror or other optical components configured to direct light from the light element 516, which is mounted to the substrate of the circuit assembly 511, downward into an opening the solenoid head 518. The light from the light element 516 may then pass through the membrane 524 and nozzle 528 as described above with respect to FIG. 11.

Figure 13B:
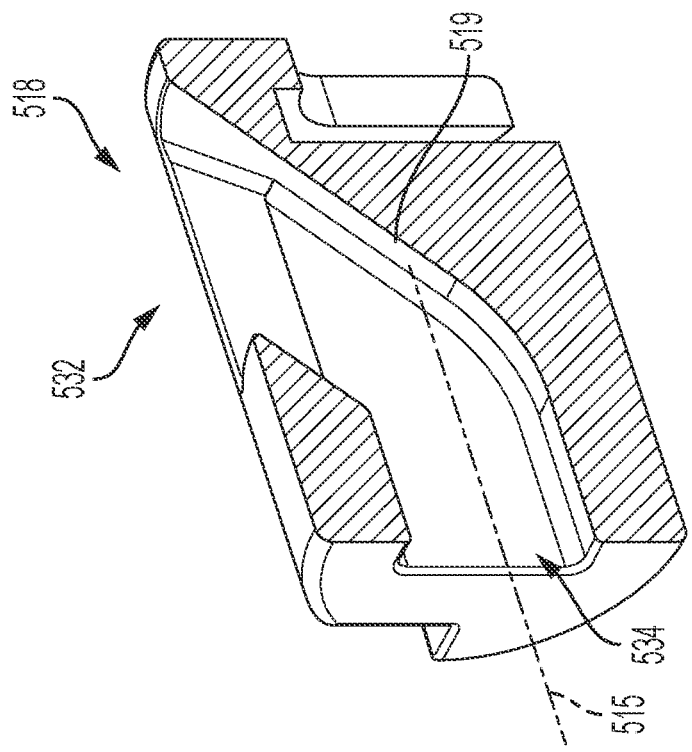
FIG. 13B is a cross-sectional view of the light guide component of FIG. 13A, according to at least one embodiment of the present disclosure.
Figure 13A:
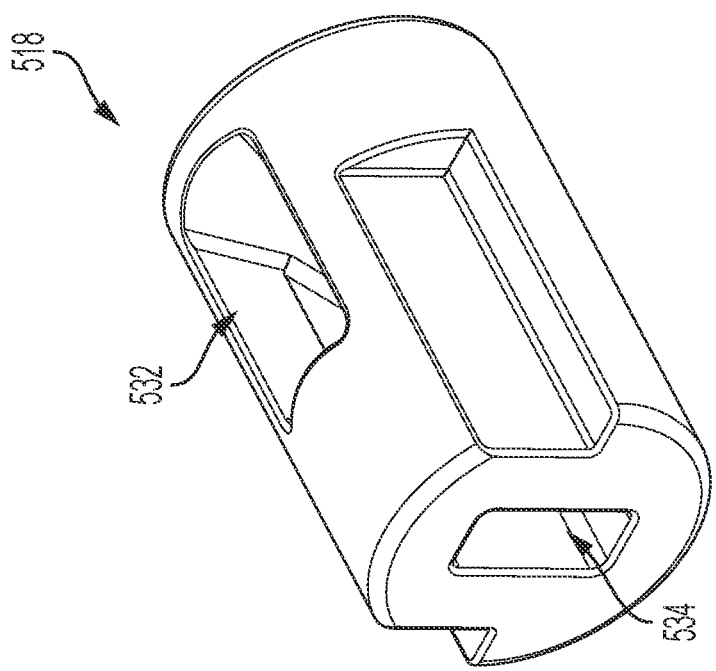
FIG. 13A is a perspective view of a light guide component of an ocular pharmaceutical applicator, according to at least one embodiment of the present disclosure.

FIGS. 13A and 13B illustrate a piston head 518 including an angled reflective surface 519 for directing light from a light element (e.g., 516, FIG. 12) out a distal opening 534 along a stream axis 515. The piston head 518 may be referred to as a light directing element, in some aspects. The light direction element 518 includes a first opening 532 on a top lateral side of the element 518, and a second opening or distal opening 534 at a distal side of the element 518. FIG. 13B is a cross-sectional view of the element 518, which includes an angled reflective surface 519 in an interior of the element 518. The element may comprise a polymer, and may be injection molded such that the surface 519 is smooth and glossy to produce coherent reflections of light out the distal opening 534. As explained above, the element 518 is configured to reflect light along the axis 515, which is parallel or co-extensive with the stream axis of the nozzle (e.g., 528, FIG. 12).

Figure 14:
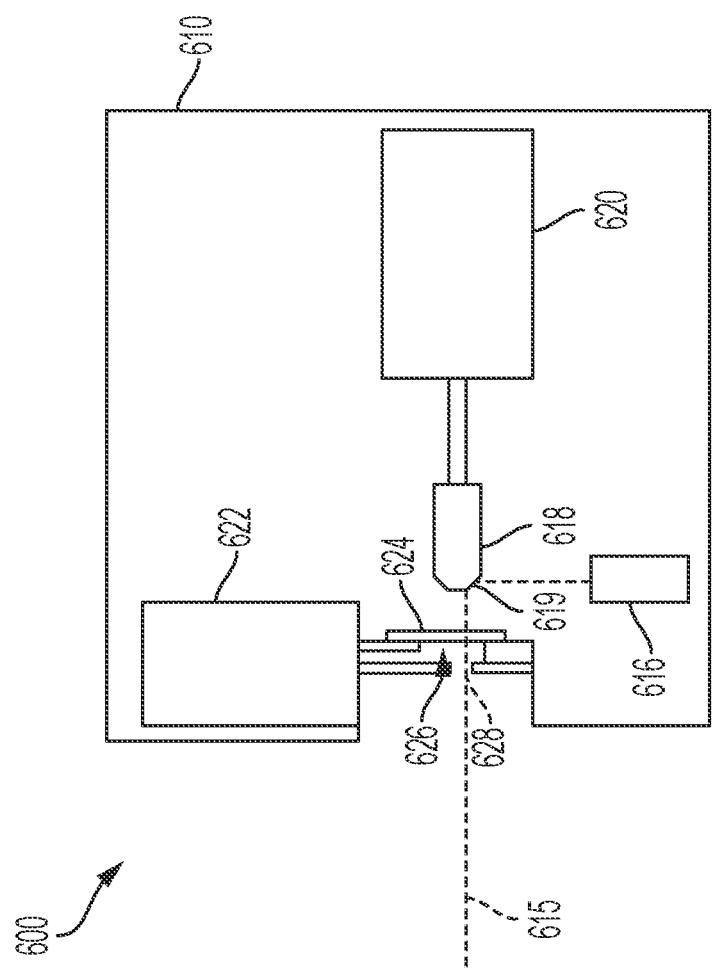
FIG. 14 is a diagrammatic view of an example ocular pharmaceutical applicator according to at least one embodiment of the present disclosure.

FIG. 14 is a diagrammatic view of an ocular pharmaceutical applicator 600, according to an embodiment of the present disclosure. Similar to the embodiment of FIG. 11, the applicator 600 includes a housing or enclosure 610 that contains a reservoir 622 containing a pharmaceutical fluid, an actuator 620, and a light source 616. In the illustrated embodiment, the actuator 620 is configured to impinge or strike the membrane 624 directly to expel the fluid in the chamber 626 out through the nozzle or slit 628. As similarly described above, the chamber 626 can be filled with the pharmaceutical fluid from a drug reservoir 622. In some embodiments, the drug reservoir 622 includes a replaceable cartridge or bottle that includes the chamber 626, membrane 624, and nozzle 628. In an exemplary embodiment, the actuator 620 comprises a solenoid, where the head 618 of the solenoid piston is sized and shaped to deform the membrane 624 into the chamber 626. In the embodiment of FIG. 14, a reflective diagonal surface 619 is positioned on an exterior angled surface of the head 618. In the illustrated embodiment, the diagonal surface 619 is oriented at an angle of 45 degrees relative to the dispensing axis of the slit 628. However, other configurations are also contemplated. For example, the diagonal surface 619 may be oriented at angles other than 45 degrees, both greater and smaller. Additionally or alternatively, the light source 616 may be offset from the head 618 of the piston such that the axis of the light source 616 is oblique to the dispensing axis of the nozzle 628.

In some embodiments, the light source 620 includes focusing optics, baffles, or other optical components configured to limit the angular dispersion of the beams of light generated by the light source 620. In the illustrated embodiment, the beam 615 is configured to reflect off the reflective surface 619 when the actuator 620 is in a retracted state. In other embodiments, the light source 620 may be configured to direct the beam 615 of light toward the reflective light when the actuator 620 is at other stages of actuation. In some embodiments, the shape of the chamber 626 matches a shape or profile of the head 618 such that the membrane 624 is deformed to contact an opposing internal surface of the chamber 626 to force a greater portion of the fluid within the chamber 626 through the nozzle 628.

The devices described herein may comprise additional or alternative components, form factors, or sub assemblies. For example, an ocular pharmaceutical applicator may comprise a form factor as described in U.S. Publication No. 2020/0360180, titled "Non-Gravitational Fluid Delivery Device for Ophthalmic Applications," filed May 13, 2020, the entirety of which is incorporated by reference herein.

As will be readily appreciated by those having ordinary skill in the art after becoming familiar with the teachings herein, the ocular pharmaceutical applicator permits even inexperienced users to apply ophthalmic medications directly to the eye with high precision, repeatability, and probability of success. Accordingly, it can be seen that the ocular pharmaceutical applicator fills a long-standing need in the art, by overcoming the drawbacks of existing eye medication delivery systems.

In embodiments that include a processor, the processor may comprise any combination of general-purpose computing devices, reduced instruction set computing (RISC) devices, application-specific integrated circuits (ASICs), field programmable gate arrays (FPGAs), or other related logic devices, including mechanical and quantum computers. In some embodiments, the processor comprises a memory in which instructions or information are stored, and the processor operates based on the instructions or information. The memory may be co-located on the same board or chip with processing elements or else located external to a board or chip containing processing elements. The memory may comprise any combination of read-only memory (ROM), programmable read-only memory (PROM), electrically erasable read-only memory (EEPROM), magnetic or electronic random access memory (RAM), flash memory, removable media, or other related memory types.

In embodiments that include external communication, including but not limited to software updates, firmware updates, or readings from the device, communication to and from the device could be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information.

Communication, if any, within or between internal electronic components of the ocular pharmaceutical applicator may be through numerous methods or protocols. Serial communication protocols may include but are not limited to SPI, I²C, RS-232, RS-485, CAN, Ethernet, ARINC 429, MODBUS, MIL-STD-1553, or any other suitable method or protocol. Parallel protocols including but not limited to ISA, ATA, SCSI, PCI, IEEE-488, IEEE-1284, and other suitable protocols. Where appropriate, serial and parallel communications may be bridged by a UART, USART, or other appropriate subsystem.

A number of variations are possible on the examples and embodiments described above. For example, the ocular pharmaceutical applicator may include an eyeblink detection system, a color-changing LED, or a dimmable LED. The system may be used to deliver drugs to other systems or orifices of the body, including the nose, mouth, and ears. The device may be employed in veterinary medicine, or may be used to deliver precise quantities of an aerosolized substance for non-medical use, including but not limited to adhesives, lubricants, paints, and dyes.

Accordingly, the logical operations making up the embodiments of the technology described herein are referred to variously as operations, steps, objects, elements, components, or modules. Furthermore, it should be understood that these may occur or be performed in any order, unless explicitly claimed otherwise or a specific order is inherently necessitated by the claim language.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the ocular pharmaceutical applicator. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

Generally, any creation, storage, processing, and/or exchange of user data associated the method, apparatus, and/or system disclosed herein is configured to comply with a variety of privacy settings and security protocols and prevailing data regulations, consistent with treating confidentiality and integrity of user data as an important matter. For example, the apparatus and/or the system may include a module that implements information security controls to comply with a number of standards and/or other agreements. In some embodiments, the module receives a privacy setting selection from the user and implements controls to comply with the selected privacy setting. In other embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations.

The above specification, examples and data provide a complete description of the structure and use of exemplary embodiments of the ocular pharmaceutical applicator as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. For example, different types of power sources may be used to power electronics, including batteries, solar cells, springs, and external "wall current".

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. A fluid dispensing device, comprising:
   an applicator body comprising:
      a light source;
      an actuator;
      an opening; and
      a reflective surface; and
   a cartridge removably positioned within the applicator body, wherein the cartridge comprises:
      a nozzle comprising an aperture;
      a membrane configured to allow a portion of light from the light source through to the nozzle;
      a fluid chamber positioned between the membrane and the nozzle; and,
      a fluid reservoir in fluid communication with the fluid chamber;
   wherein the light source is configured to emit a beam in a first direction, and wherein the reflective surface is configured to redirect the beam in a second direction such that the beam passes through the membrane, the fluid chamber, and the aperture in the nozzle; and
   wherein the actuator is configured to depress the membrane into the fluid chamber thereby causing fluid to be expelled from the fluid chamber through the aperture in the nozzle such that a stream of fluid is expelled from the fluid chamber through the aperture along a path of the beam.

2. The device of claim 1, wherein the light source comprises an aligned baffle having a first slit width, and wherein the nozzle has a second slit width, and wherein the first slit width and the second slit width are less than 400 micrometers (μm).

3. The device of claim 1, wherein the beam of light is visible to a human eye if the nozzle is aimed at the human eye within a rotational precision below ±8.5 degrees when the device is positioned for fluid delivery about 15 mm from the eye.

4. The device of claim 1, wherein the aperture of the nozzle comprises two adjacent slits less than 1 mm apart that are positioned and aligned to allow light through to a user so that when the nozzle is aligned to a human eye light through both slits are equally perceived in intensity.

5. The device of claim 1, wherein the light source comprises a first light-emitting diode (LED).

6. The device of claim 1, wherein the light source comprises an integrated LED surface mount package of two or more single color LED dies situated in a single line, wherein the LED surface mount package is configured to change from a first color to a second color without impacting an angle of the light along the path of the beam.

7. The device of claim 1, further comprising:
   a range sensor; and
   a processor in communication with the range sensor,
   wherein the processor is configured to:
      determine, using information from the range sensor, whether a range between the nozzle and a human eye is greater than a threshold amount;
      in response to determining that the range is greater than the threshold amount, change a visual property of the light source to a first value; and
      in response to determining that the range is less than the threshold amount, change the visual property of the light source to a second value.

8. The device of claim 1 wherein the applicator body further comprises:
   at least one brow rest configured to contact a user's eyebrow ridge; and
   at least one cheekbone rest configured to contact a user's cheekbone,
   such that when the brow rest is contacting the user's eyebrow ridge and the cheekbone rest is contacting the user's cheekbone, the light source is visible to the user's eye through the nozzle.

9. The device of claim 1, wherein the actuator comprises a piston and a head coupled to a distal end of the piston, wherein the head is configured to contact the membrane in an actuated position, and wherein the head comprises the reflective surface positioned with respect to the light source such that the beam from the light source is reflected through the nozzle.

10. The device of claim 9, wherein the head comprises a first opening adjacent to the light source, and a second opening at a distal end of the head, wherein the reflective surface is within the head such that the portion of light enters through the first opening, reflects off the reflective surface, and propagates out of the second opening.

11. The device in claim 9, wherein the applicator body further comprises one or more photodetectors, and wherein the photodetectors are configured to detect a presence or location of the actuator based on internal reflection of the light off of the head from the light source.

12. The device of claim 1, wherein an applicator body comprises an activation button, the light source, and the actuator.

13. The device of claim 1, further comprising an actuatable nozzle cover coupled to the applicator body and configured to cover the nozzle.

\* \* \* \* \*